(12) United States Patent
Sarkar

(10) Patent No.: US 10,938,885 B2
(45) Date of Patent: Mar. 2, 2021

(54) MOBILE FILE TRANSFER METHODS AND APPARATUS

(71) Applicant: New York Blood Center, Inc., New York, NY (US)

(72) Inventor: Sabyasachi Sarkar, Morganville, NJ (US)

(73) Assignee: New York Blood Center, Inc., New York, NY (US)

( * ) Notice: Subject to any disclaimer, the term of this patent is extended or adjusted under 35 U.S.C. 154(b) by 531 days.

(21) Appl. No.: 15/480,110

(22) Filed: Apr. 5, 2017

(65) Prior Publication Data

US 2017/0295219 A1    Oct. 12, 2017

Related U.S. Application Data

(60) Provisional application No. 62/319,054, filed on Apr. 6, 2016.

(51) Int. Cl.
| | | |
|---|---|---|
| *H04L 29/08* | (2006.01) | |
| *G06F 16/182* | (2019.01) | |
| *G16H 10/60* | (2018.01) | |
| *G06F 16/16* | (2019.01) | |

(52) U.S. Cl.
CPC .......... *H04L 67/06* (2013.01); *G06F 16/168* (2019.01); *G06F 16/182* (2019.01); *G16H 10/60* (2018.01); *H04L 67/2833* (2013.01); *Y02A 90/10* (2018.01)

(58) Field of Classification Search
None
See application file for complete search history.

(56) References Cited

U.S. PATENT DOCUMENTS

| | | | | |
|---|---|---|---|---|
| 9,730,073 | B1* | 8/2017 | Kuehnel | H04W 12/08 |
| 2003/0040835 | A1* | 2/2003 | Ng | A61M 1/387 |
| | | | | 700/214 |
| 2010/0049542 | A1* | 2/2010 | Benjamin | G06Q 10/0637 |
| | | | | 705/2 |
| 2012/0324067 | A1* | 12/2012 | Hari | G06F 13/385 |
| | | | | 709/222 |
| 2015/0351004 | A1* | 12/2015 | Ko | H04W 48/10 |
| | | | | 455/411 |
| 2016/0328521 | A1* | 11/2016 | Mickles | G16H 10/60 |
| 2018/0039748 | A1* | 2/2018 | Case | G06Q 10/087 |

* cited by examiner

*Primary Examiner* — Mohamed Ibrahim
(74) *Attorney, Agent, or Firm* — K&L Gates LLP; Louis C. Cullman; Dennis A. Majewski

(57) ABSTRACT

A system, method, and apparatus for transferring blood donation files are disclosed. An example system includes a collection device located at a blood donation site and a collection server located in a remote location. The example collection device is configured to store blood donation information from blood donors within a blood donation batch file located at a designated directory of a memory, and store metadata related to the blood donation information to the blood donation batch file. The example collection device also transmits the blood donation batch file to a registered user device. The example collection server is configured to determine the registered user device is available via a network connection. Responsive to determining the user device is connected, the collection server acquires the blood donation batch file from the user device and aggregates the blood donation batch file with blood donation batch files received from other registered user devices.

20 Claims, 8 Drawing Sheets

| | File Name | Size | Collected | Received | Via Phone |
|---|---|---|---|---|---|
| ☐ | | | | | |
| ☑ | File A | 4K | 9:01 AM | 9:11 AM | Jim |
| ☑ | File B | 6K | 9:22 AM | 10:11 AM | Jill |
| ☑ | File C | 5K | 9:23 AM | 10:11 AM | Jim |
| ☐ | File D | | | | |
| ☑ | File E | 5K | 9:23 AM | 10:11 AM | Jim |
| ☑ | File F | 5K | 9:23 AM | 10:11 AM | Jim |

Management Console: Progress — 702
Laptop A | Laptop B | Laptop C
700

FIG. 7

MOBILE FILE TRANSFER METHODS AND APPARATUS

PRIORITY CLAIM

The present application claims priority to and the benefit of U.S. Provisional Patent Application Ser. No. 62/319,054, filed on Apr. 6, 2016, the entirety of which is incorporated herein by reference.

BACKGROUND

Wireless networks have seemingly become ubiquitous in the United States as well as most of the developed world. For instance, many people take for granted that their smartphone, tablet, or laptop computer can connect to a Wi-Fi or 3G/4G/5G network in almost any location. Constant access to email, feature-rich websites, and steaming media content may almost be considered a basic necessity. As a result, most connectivity solutions assume that network access is constantly available.

However, there are still some instances where devices may not have access to a network connection at all, or at best, an unreliable wireless connection. For instance, dense urban areas still have pockets (e.g., basement areas, interior office spaces, subway systems, etc.) where network access is unavailable or less than desirable. These urban locations generally do not have access to 3G/4G/5G wireless networks due to signal degradation resulting from building infrastructure that acts as a signal shield. Further, many of these locations are not accessible to or have Wi-Fi networks due to infrequent use. Some interior spaces may have Wi-Fi or hardline Internet access, but this access is usually restricted to authorized devices. Guest network connections may not be available. Even when a guest network connection is present, receiving credentials to access the network can be cumbersome and network firewalls may not be compatible with network settings on the guest devices without substantial modification or some IT training.

In an example, urban blood drives often take place in the subterranean floors or interior spaces of large office buildings. Blood information collection devices (e.g., laptops, workstations, portable servers, etc.) acquire blood donation information during the blood drive. The blood donation information is used by a central server for processing, testing, and approving the donated blood before it can be made available to hospitals and clinics. The lack of network access during blood drives makes data transfer to the central server difficult. Some known solutions require that the blood collection devices be physically connected to the central server (or connected to a secure local network that is also connected to the central server). Other known solutions require that Universal Serial Bus ("USB") memory sticks be used to transfer donor blood data between the blood collection devices and the central server. As one can appreciate, physically moving a collection device or a memory stick to the central server is time consuming, inefficient, and unreliable. Memory sticks can be lost (or stolen) or collection devices may be deployed in the fields for weeks before there is an opportunity to connect to the central server. In addition, physical transfer of sensitive and private blood donation information requires robust and secure tracking and transportation processes. As a result, such known processes are generally unacceptable, inefficient, and costly for transferring sensitive donor blood data in a timely manner to facilitate the use of donated blood.

SUMMARY

The present disclosure provides a new and innovative system, method, and apparatus for transferring files between two locations (such as a blood donation site and a collection server) when a continuous communication link does not exist between the locations. The system, method, and apparatus disclosed herein are configured to use an intermediary portable device, such as a smartphone or tablet computer, that bridges the communication gap between the two locations. The example system, method, and apparatus disclosed herein use one or more file transfer applications that coordinate the transfer of files between the two locations using the intermediary portable device such that duplicate copies of the same file are not sent to the destination location. The transfer of the files may be provided through a secure connection to ensure file data is not compromised or accessed improperly.

In an example embodiment, a collection server is configured to determine whether there exists any Internet connection to a remotely located local collection device that is configured to store blood donation information within a batch file having metadata related to (i) the blood donation information and (ii) a status of the batch file. Responsive to determining that an Internet connection to the local collection device does not exist, the collection server determines whether there exists any Internet connection to a remotely located user device that is configured to store a copy of the batch file at the local collection device. Responsive to determining that an Internet connection exists, the collection server acquires metadata of the copy of the batch file from the user device via the Internet connection. The example collection server compares the metadata of the copy of the batch file to metadata of other batch files locally stored at the collection server. Responsive to determining that the metadata does not match the metadata of the other batch files, the collection server acquires the copy of the batch file from the user device via the Internet connection. The collection server may then publish information related to the metadata within a dashboard including an identifier of the user device from which the copy of the batch file was received.

In another embodiment, a system for transferring blood donation batch files includes a collection device, a central collection server, and one or more user devices. The collection device is configured to receive blood donation information from blood donors and store the blood donation information within a blood donation batch file located at a designated directory of a memory. The collection device is also configured to receive or create metadata related to the blood donation information and the blood donation batch file, store the metadata to the blood donation batch file, and make the blood donation batch file available at the designated directory. The one or more user devices are configured as trusted registered devices of the collection system and are configured to operate respective transfer applications. Each of the transfer applications is configured to determine whether the respective user device is communicatively coupled to the collection device via a local connection. Responsive to determining that the collection device is connected, the transfer application is configured to acquire the blood donation batch file from the designated directory of the collection device and store the blood donation batch file to a memory of the user device. The central collection server is configured to determine the user device is available via a network connection and responsive to determining the user device is connected, acquire the blood donation batch file from the user device. The central collection server aggregates the blood donation batch file with blood donation batch files received from other user devices.

Additional features and advantages of the disclosed system, method, and apparatus are described in, and will be apparent from, the following Detailed Description and the Figures.

BRIEF DESCRIPTION OF THE FIGURES

FIG. 7 shows a diagram of an example graphical representation of batch file metadata displayed within a user interface, according to an example embodiment of the present disclosure.

DETAILED DESCRIPTION

Figure 1:
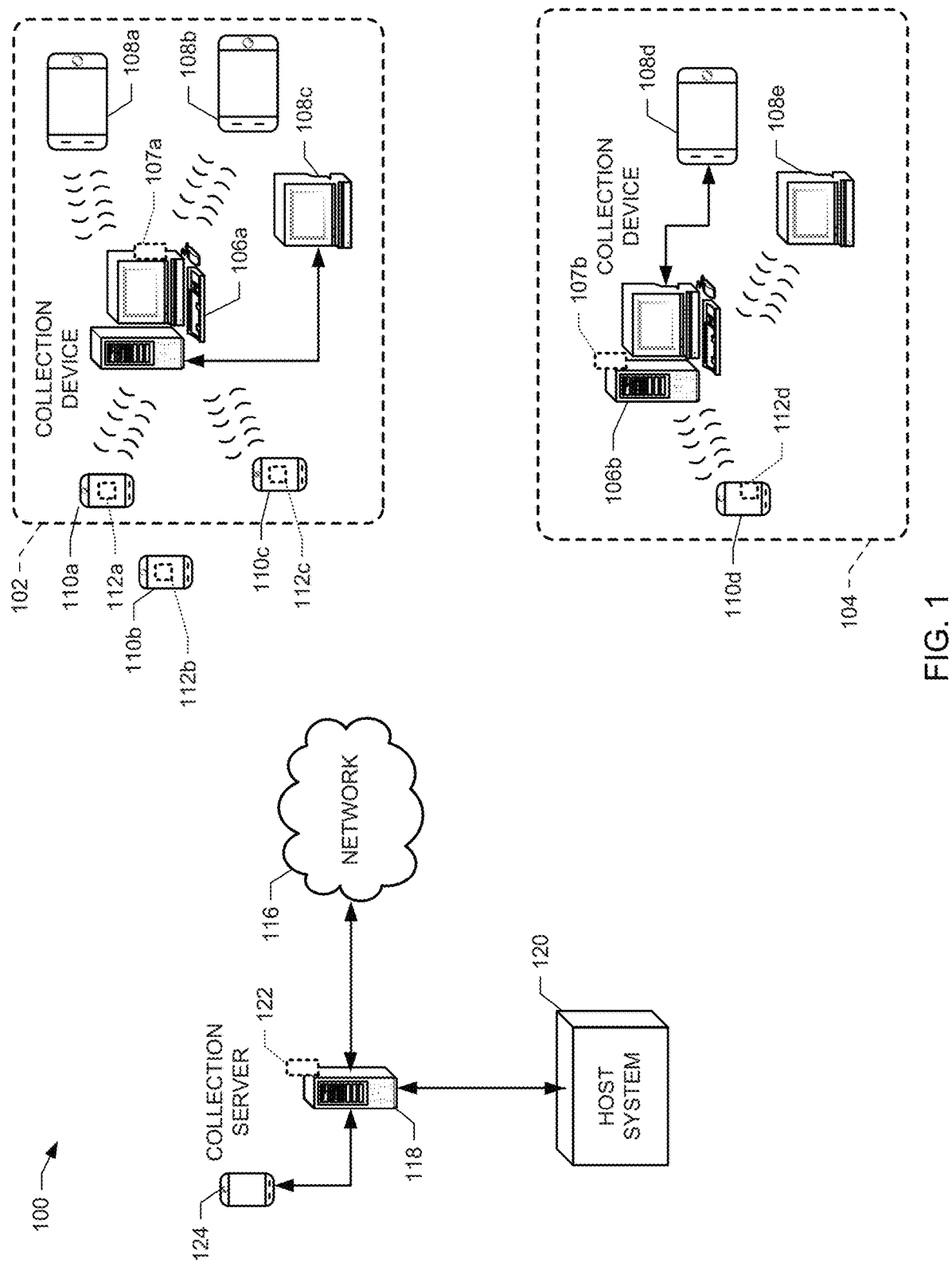
FIGS. 1 to 3 show diagrams of a mobile file transfer environment, according to an example embodiment of the present disclosure.

The present disclosure relates in general to a method, apparatus, and system for transferring files from a first location to a second location when a continuous network connection does not exist. The method, apparatus, and system disclosed herein use user devices, such as smartphones, smartwatches, smart-eyewear, or tablet computers as an intermediary node to transfer one or more files from a laptop or other workstation located in a first location with limited or no network access to a centralized file collection server located in a second location. The example laptops, user devices, and centralized collection server are configured to perform file verification and synchronization to reduce or eliminate duplicate or redundant file transfers and ensure that the content of the files remains identical or consistent through the transfer. The example laptops, user devices, and centralized collection server are configured to communicate via secure network connections through public networks and may use one or more encryption methods to protect the files during transfer.

The example method, apparatus, and system disclosed herein are described in connection with the transfer of blood donation information collected during blood drives. However, it should be appreciated that the file transfer method, apparatus, and system disclosed herein is not limited to such an application. In other embodiments, the example method, apparatus, and system disclosed herein may be applied to other file transfer applications, such as military applications, first responder applications, medical applications, utility technician applications, or any other situation where a continuous network connection does not exist between devices located at two separate locations.

As mentioned above, mobile blood drives are often located in building basements or interior rooms that have limited or no network connectivity. About 80% of all donated blood is collected through mobile blood drives compared to 20% collected at fixed dedicated sites. On average, an organization may operate approximately 50 simultaneous blood drives per day at different locations within an urban or suburban environment. The mobile blood drives typically occur in office buildings, residential buildings, schools, churches, and blood collection buses. Oftentimes, the only open space available for a blood drive is a basement, an interior space, a cafeteria, or a gymnasium. Network connectivity at these mobile sites is often inconsistent or nonexistent. For example, buildings may have cellular dead spots in the basement or interior locations due to building infrastructure acting as a signal shield or filter. Adverse weather may further weaken already weak signals and further limit connectivity. Further, some locations may not have an open or public wireless connection (e.g., Wi-Fi) to a wireless router. In instances where some locations have a guest network, configuring a laptop or smartphone to access the network may be cumbersome as a result of firewalls or authenticating processes interfering with network settings on the connecting device. In aggregate, these factors at mobile sites often create a connectivity disconnect between blood collection computing devices at the site and a centralized server or other computing entity that is only accessible by a network.

During blood drives, each donor is required to provide certain blood donation information that includes demographic information and answers to eligibility questions. In addition, blood draw information is collected while the donor is giving blood. The blood donation information for each donor is associated with an identifier that is placed on blood collection bags having blood from that donor. A centralized downstream host blood donation system uses the blood donation information to facilitate testing of the blood and make a determination as to whether the donated blood can be made available to hospitals or clinics (or discarded).

The limited network connectivity between the mobile donation sites and the centralized host blood donation system can affect how quickly and efficiently blood can be made available to hospitals or clinics. For instance, loss of connectivity (due to an inconsistent network connection) while blood donation information is being transferred may result in incomplete information being received at the centralized server. As a result, the donated blood cannot be approved and has to be discarded if the correct data is not ultimately received. To overcome this potential issue, some known blood collection agencies are forced to use USB memory sticks to physically transfer the blood donation information. However, with over 50 blood drives a day, tracking each of the memory sticks is tedious and opens up the possibility that at least some of the memory sticks could become lost or stolen, thereby resulting in donated blood being discarded. Even worse, sensitive donor information may be compromised.

To overcome these limitations, the example method, apparatus, and system disclosed herein include user devices and mobile collection devices that are specifically registered to securely transmit blood donation information. For instance, the mobile collection devices are configured to receive blood donation information from donors. The user devices are configured as communication bridges to span the communication gap between the mobile collection devices and one or more centrally-located collection servers. Specifically, the user devices are configured to connect to proximately located mobile collection devices and obtain the blood donation information. Later at a subsequent time when the user devices are no longer at the connectivity-constrained site and have a wireless (e.g., a cellular) network connection with Internet access, the user devices are configured to transfer the blood donation information to a collection server, which aggregates the information for transfer to the host blood donation system. In some instances, the mobile collection devices may not have access to the Internet but the user devices may have access to a cellular network. In these instances, the user devices may bridge the network connection gap between the mobile collection devices and the collection server via the cellular connection without having to be moved to a different location. The example collection server is also configured to manage and synchronize the file transfer to ensure the contents of the information do not change during the transfer process and to prevent duplicate information from being aggregated.

As disclosed herein, the blood donation information is stored and transferred within a blood donation batch file, or more simply, a batch file. The example method, apparatus, and system are configured to combine blood donation information from multiple donors at a collection site into a single batch file for transmission to the host blood donation system. Each batch file includes metadata, which may provide information related to a number of blood donors, a last update time of the batch file, a file size of the batch file, a file identifier of the batch file, a creation date/time of the batch file, and/or an identifier of the user device used to transfer the batch file.

The transfer of a batch file to a user device causes a copy of the batch file to be stored to a user device. In some embodiments, multiple user devices may be connected to a collection device at a mobile donation site. Each user device may receive a copy of the batch file. Later, when the user devices have access to a wireless (e.g., a cellular) network connection with Internet access, the collection server makes a local copy of the batch file from one of the user devices. The collection server then prevents the copies of batch file from the other user devices to be transmitted since the collection server now has one copy of the batch file. In some embodiments, the collection server may instruct the user devices to delete or otherwise discard the copies of the batch files such that they are no longer in a directory related to file transmission. This may include instructing the user devices to transfer or more the copies of the batch files to another directory, which may be unknown to the collection server.

Mobile File Transfer Environment

FIG. 1 shows a diagram of a mobile file transfer environment 100, according to an example embodiment of the present disclosure. The environment 100 includes a first mobile blood donation site 102 and a second mobile blood donation site 104. The donation sites may include office buildings, residential buildings, public parks, schools, churches, blood donation buses, hospitals, etc. It should be appreciated that the environment 100 may include additional or fewer donation sites. For instance, the environment 100 may include 50 blood donation sites.

Each of the donation sites 102 and 104 includes a collection device 106 (e.g., a blood donation information collection device), which may include any laptop computer, workstation, personal computer, server, tablet computer, etc. The example collection device 106 is communicatively coupled to registration devices 108, which may include any laptop computer, tablet computer, interactive display screen, laptop computer, personal computer, workstation, smartphone, etc. Together, the registration devices 108 and the collection devices 106 are configured to acquire blood donation information from blood donors. For instance, the registration devices 108 may include an application defined by computer-readable instructions, which when executed by a processor, cause the registration devices to provide a user interface that prompts blood donors for specific information. In FIG. 1, registration devices 108a and 108b are tablet computers that enable users to enter demographic information and answer qualification questions through a touchscreen interface as part of the registration process for blood donation. The registration device 108c includes a laptop computer that enables a user to enter demographic information and answer qualification questions via a keyboard and mouse.

The registration devices 108 are configured to transmit the blood donation information to the collection device 106 for processing aggregation. For example, the collection device 106 may process the blood collection information through one or more filters or rules to determine if a donor is in fact eligible to donate blood. A collection application 107 operating on the collection device 106 is configured to store the blood donation information within a blood donation batch file, which also includes blood donation information related to other donors. In some embodiments, the collection application 107 may be a daemon application.

The collection device 106 is configured to be communicatively coupled to the registration devices 108 via any local network connection or direct connection. For example, the collection device 106 may include (or be communicatively coupled to) a wireless router that provides a secure local wireless (and/or wired) network. For instance, the collection device 106a may be communicatively coupled to the registration devices 108a and 108b via a secure Wi-Fi network. Additionally or alternatively, the collection device 106 may have a direct communication connection (e.g., Bluetooth®, Zigbee®, USB, NFC, etc.) to each of the registration devices 108.

The example donation sites 102 and 104 include a number of user devices 110, which may include any smartphone, smartwatch, smart-eyewear, laptop computer, or tablet computer. The user devices 110 include a collection application 112, which may comprise machine-readable instructions stored in a memory. The collection application 112 is configured to acquire one or more batch files from a proximately located collection device 106. The user devices 110 may be communicatively coupled to the collection device 106 via a secure Wi-Fi network. Additionally or alternatively, the user devices 110 may have a direct communication connection (e.g., Bluetooth®, Zigbee®, NFC, etc.) to the collection device 106.

The example environment 100 also includes a network 116, a collection server 118, and a host system 120. The example network 116 includes any cellular network (e.g., a 3G, 4G, and/or 5G wireless network), any wireless local area network ("WLAN") such as Wi-Fi, and/or any wireless or wired wide area network ("WAN") such as the Internet. In some embodiments, the network 116 may include combinations of different types of networks. For example, the network 116 may include a cellular network that is communicatively coupled to a WAN.

The example collection server 118 is communicatively coupled to the network 116 via any wired and/or wireless connection. The collection server 118 is configured as a centralized file aggregation site and includes a management application 122 configured to manage the secure acquirement of batch files from the user devices 110. As discussed in more detail below, the collection server 118 may also provide a dashboard or other management user interface that enables blood donation personnel to view a status and/or location of batch files. For instance, management user device 124 may access the collection server 118 to view a status and/or content of batch files.

The example host system 120 (e.g., a centralized downstream host blood donation system) is configured to process the blood donation information of the batch files to enable testing and inventory management of donated blood. For instance, the host system 120 may track blood samples of donated blood as the samples are tested for certain diseases and conditions. The host system 120 uses a unique identifier to track which blood samples and donated blood correspond to which blood donation information. The host system 120 may also determine which donated blood may be added to a blood bank or determine a match to a potential blood recipient.

In some instances, either or both of the collection server 118 and/or the host system 120 may be distributed within a cloud computing environment. For example, the collection server 118 may include a scalable file storage system in addition to one or more management interfaces. In other examples, collection servers 118 may be located at predetermined geographic locations to reduce transmission time with user devices 110.

In the illustrated example of FIG. 1, the donation sites 102 and 104 do not have a connection to the network 116. For instance, the donation sites 102 and 104 may be located in a building basement or interior room. Accordingly, the collection devices 106 are not able to communicatively couple to the collection server 118 via the network 116. However, the collection devices 106, during this time, receive and locally store blood donation information in one or more batch files.

To facilitate transmission to the collection server 118, the collection devices 106 are configured to transmit the blood donor batch files to the proximate user devices 110. For example, the user devices 110a and 110c detect they are communicatively coupled to the collection device 106a at the donation site 102. The respective transfer application 112a and 112c of the user devices 110a and 110c read a designated memory or directory location of the collection device 106a. The transfer applications 112a and 112c determine whether any of the batch files at the designed directory are new and/or have been updated since a previous transfer. For instance, the transfer applications 112a and 112c may read metadata of the batch files and compare the metadata to metadata of batch files already stored at the user devices 112a and 112c. If there are new or updated batch files, the example transfer applications 112a and 112c are each configured to acquire a copy of the new and/or updated batch files from the collection device 106a located at the donation site 102. The transfer applications 112a and 112c may update or supplement the metadata of the received batch files with user device-specific information. For example, the transfer applications 112a and 112c may update the metadata with an identifier of the user device and/or a time a copy of the batch file was stored at the respective user devices 110a and 110c.

Figure 2:
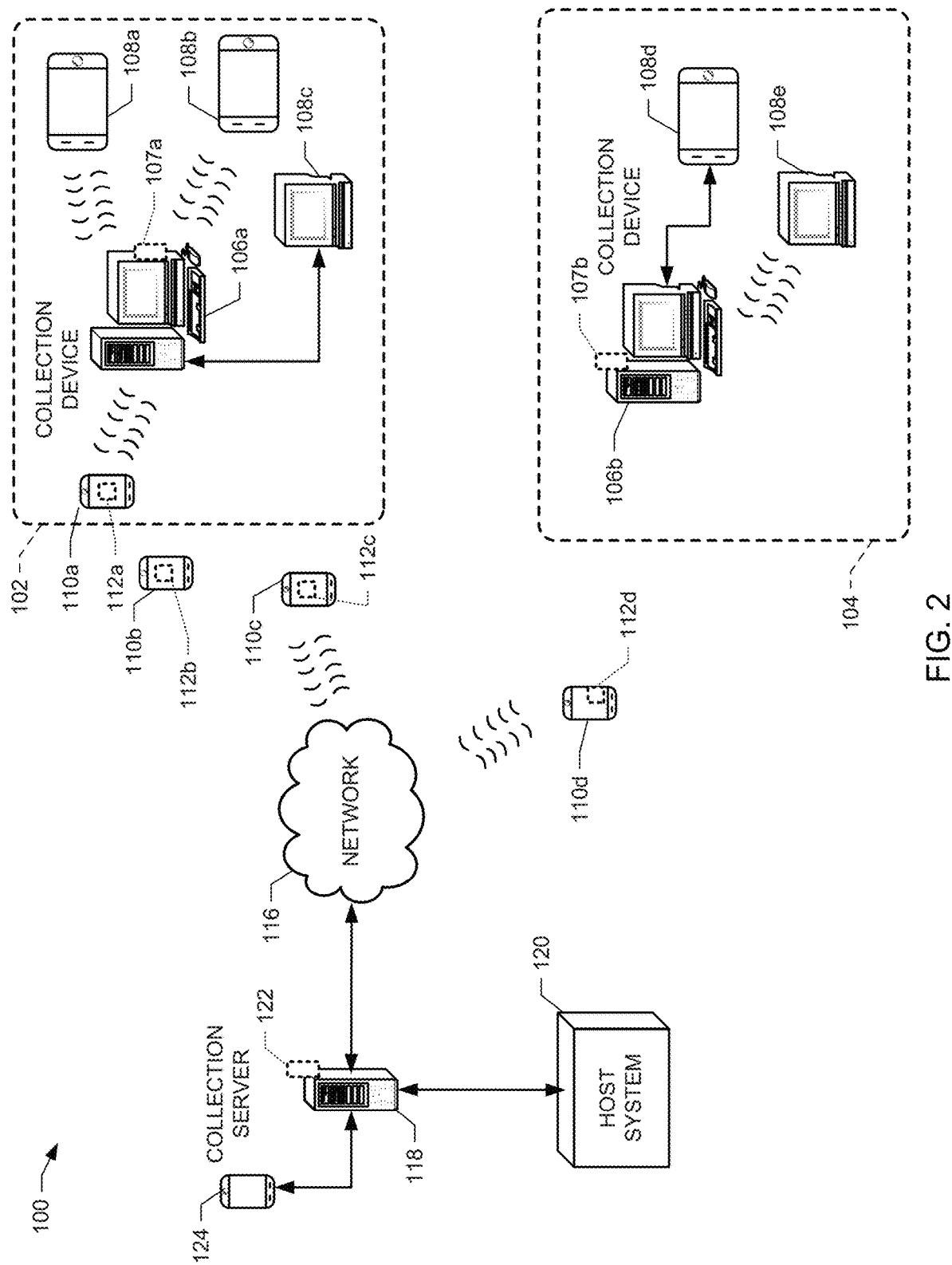

In the illustrated embodiment of FIG. 1, the user devices 110a and 110c are also not communicatively coupled to the network 116 while they are located at the collection site 102. For instance, the user devices 110a and 110c may not have access to a cellular network. However, as shown in FIG. 2, at some subsequent time (e.g., 5 minutes, 10 minutes, 60 minutes, etc.) from the embodiment shown in FIG. 1, user of the user device 110c leaves the donation site 102. The user may leave during a lunch break or to obtain more supplies, for example. After leaving the donation site 102, the user device 110c obtains a connection to the network 116, which may include a connection to a 3G/4G/5G cellular network. After connecting to the network, the transfer application 112c transmits a notification message to communicatively couple to the collection server 118. In other examples, the collection server 118 may periodically transmit ping messages to detect when the user device 110c is communicatively coupled to the network 116.

After detecting that the user device 110c is connected to the network 116, the example management application 122 is configured to read which batch files are stored at the user device 110c. In some embodiments, the management application 122 may request that the transfer application 112c provide metadata related to locally stored batch files. The management application 122 compares the received metadata to metadata of already received batch files to determine which batch files at the user device 110c are new and/or updated. The management application 122 of the collection server 118 acquires copies of the batch files that are new and/or updated from the user device 110c via the transfer application 112c. After confirming that the entire contents of the batch files have been copied (e.g., through a checksum verification or metadata comparison), the management application 122 may transmit a delete message to the user device 110c. Upon receiving the delete message, the transfer application 112c is configured to delete, discard, or make the specified batch files hidden from future transmission to the collection server 118. In some instances, the transfer application 112c may store a copy of the metadata of the deleted batch files to later determine (when the user device 110c is back at the donation site 102) which batch files have already been received from the collection device 106.

In some embodiments, the management application 122 may not transmit a delete message. Instead, the management application 122 may transmit an acknowledgement message indicative that specified batch files have been successfully transferred. The user device 110c retains the transferred batch files as evidence of files that have already been transferred. This may prevent the collection application 107 and/or the transfer application 112 from transmitting the same batch files from the collection device 106 that have already previously been transferred to the user device 110. In these embodiments, the user devices 110 may retain the batch files until a blood donation session has ended and/or until after a specified time period (e.g., a week, a month, two months, etc.).

The example management application 122 of the collection server 118 is configured to make the received batch files available for display within a dashboard or other graphical interface. The management application 122 may display for the management user device 124 a list of received batch files including at least some of the metadata, which may comprise an identifier of the user device 110c. The metadata enables tracking of the batch files. The management application 122 also aggregates the batch files for transmission to the host system 120.

In the illustrated example of FIG. 2, it should be appreciated that the user device 110a also has a copy of the batch files that were transmitted by the user device 110c to the collection server 118. The example management application 122 is configured to ensure that the collection server 118 does not receive a duplicate of the same batch files from the user device 110a. For instance, the user of the user device 110a may leave the donation site 102 at some later time after the user of user device 110c has left. The collection server 118 detects that the user device 110a is now connected to the network 116. The management application 122 of the collection server 118 requests to read the metadata of the batch files stored on the user device 110a. The management application 122 determines that the metadata received from the user device 110a matches (or at least partially matches) metadata of batch files already previously received (from the user device 110c). As a result of this determination, the management application 122 may transmit a delete message to the user device 110a instructing the transfer application 110a to delete, discard, or otherwise hide the batch files from transmission. Such a configuration ensures that the collection server 118 only receives one copy of batch files stored at the collection device 106a. In other instances, the management application 122 may transmit a message indicative that the batch files have already been transferred. It should be appreciated that the above-described configuration creates a race among the user devices 110 such that the first one to establish a connection to the network 116 is the device that usually transmits a copy of the batch files to the collection server 118.

Also as shown in FIG. 2, the example user device 110d connects to the network 116. As described above in connection with the user device 110c, the collection server 118 acquires a copy of the batch files from the user device 110d in the same manner. While the user device 110d is out of communication range, the collection device 106b has to wait until the user device 110d returns to the donation site 104 before new and/or updated batch files can be transmitted. By comparison at donation site 102, the collection device 106a may continue to provide new batch files or updates to batch files to the user device 110a while the other user device 110c is out of range.

In some embodiments, the transfer applications 112 of the user devices 110 may communicate with each other. In the example of FIG. 2, after transmitting a copy of certain batch files to the collection server 118, the user device 110c may return to the donation site 102. The transfer application 112c of the user device 110c detects that the user device 110a is on a same local network or is in proximity for a direct connection. After connecting, the transfer application 112c transmits a message to the transfer application 112a of the user device 110a that includes, for example, metadata of batch files already transmitted to the collection server 118. After receiving the message, the transfer application 112a determines if any batch files match the received metadata. The transfer application 112a then deletes, discards, or otherwise prevents the batch files with the matching metadata to be made available to the collection server 118.

In other embodiments, the management application 122, the transfer application 112, and/or the collection application 107 may be configured for parallel transmission of batch files to improve transmission speed. For example, the transfer applications 112a and 112c and/or the collection application 107 may designate certain batch files or portion of batch files to be transmitted to one user device (e.g., the user device 110a) while other batch files or portions of batch file are to be transmitted to another device (e.g., the user device 110c). The exact device may not be specified. Instead, the designation may be based on which user device first connects to the collection device 106. The transfer applications 112a and 112c and/or the collection application 107 then manage the copying of the specified batch files or portions of batch files to the first to connect user device (e.g., user device 110a) while the other batch files or portions of batch files are queued for transmission to the next user device that connects (e.g., the user device 110c). In these other embodiments, both of the user devices 110a and 110c may need to eventually connect to the collection server 118 for all of the batch files to be transferred.

In another embodiment, the transfer applications 112a and 112c and/or the management application 122 may be configured to coordinate the transfer of batch files or portion of batch files from the user devices 110a and 110c to the collection server 118. For instance, the management application 122 may detect at roughly the same time that the two user devices 110a and 110c are newly connected to the network 116. For instance, the collection server 118 may poll every 5 minutes for user devices 110. The management application 122 may determine that the user devices 110a and 110c include the same batch files. The management application 122 may partition the batch files or portions of the batch files such that some are sent from the user device 110a while others are sent from the user device 110c.

Figure 3:
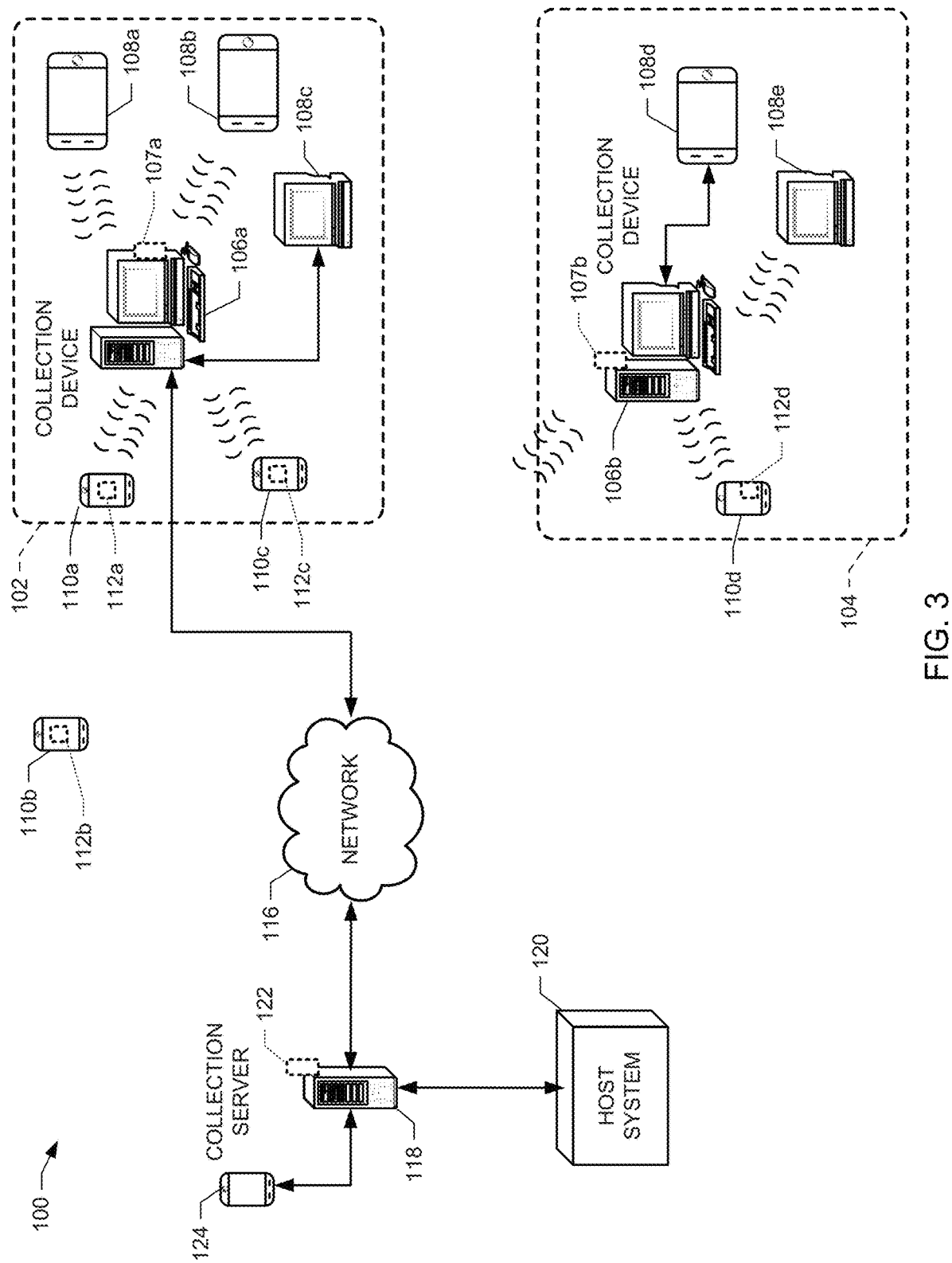

FIG. 3 shows a diagram of the mobile file transfer environment 100 of FIG. 1 when one of the collection devices 106 has a connection to the network 116, according to an example embodiment of the present disclosure. In this illustrated example, the collection device 106a has a wired Internet connection to the network 116 and the collection server 118. In other examples, the collection device 106a may have a wireless connection to the network 116.

The example management application 122 is configured to detect that the collection device 106 is connected to the network 116. For instance, the management application 122 may periodically transmit ping or poll messages based on a list of MAC IDs, IP addresses, and/or other identifiers of user devices 110 and collection devices 106. Responsive to receiving a response, the management application 122 determines that the collection device 106 is connected. Additionally or alternatively, the collection device 106 (e.g., via the collection application 107) may establish a secure connection (e.g., a VPN connection) to the collection server 118 via the network 116 after connecting to the network 116. After the management application 122 detects the connection, the management application 122 is configured to acquire metadata of batch files stored at a designed directory at the collection device 106a. The management application 122 compares the received metadata to metadata of already received batch files and determines if any of the remotely located batch files at the collection device 106 are new and/or updated. The management application 122 receives a copy of the new and/or updated batch files from the collection device 106. Subsequently, when the user devices 110a to 110c attempt to connect to the collection server 118, the management application 122 is configured to determine that the batch files have already been received from the collection device 106. The management application 122 may also cause those copies of batch files on the user devices 110a to 110c to be deleted, discarded, or otherwise removed from transmission. In other instances, the collection device 106a may not make batch files available for transmission to the user devices 110a to 110c if they have already been transmitted to the collection server 118. For example, the collection device 106a may move transmitted batch files to another directory location (hidden from or unknown to the user devices 110a to 110c) or change a flag in the metadata of the batch files to 'transmitted to collection server' (e.g., set a transmission flag).

In other instances, the collection device 106 and/or the user device 110 may retain the batch files in the same directory location after transfer without using a flag indicative of transmission. In these other instances, the retained presence of the batch files on the collection device 106 and/or the user device 110 is used to determine that copies of the files are no longer needed for transfer. For example, the user device 110 may compare metadata from the collection device 106 to metadata of already stored batch files to determine which batch files are new and/or updated.

Mobile File Transfer Application Embodiment

Figure 4:
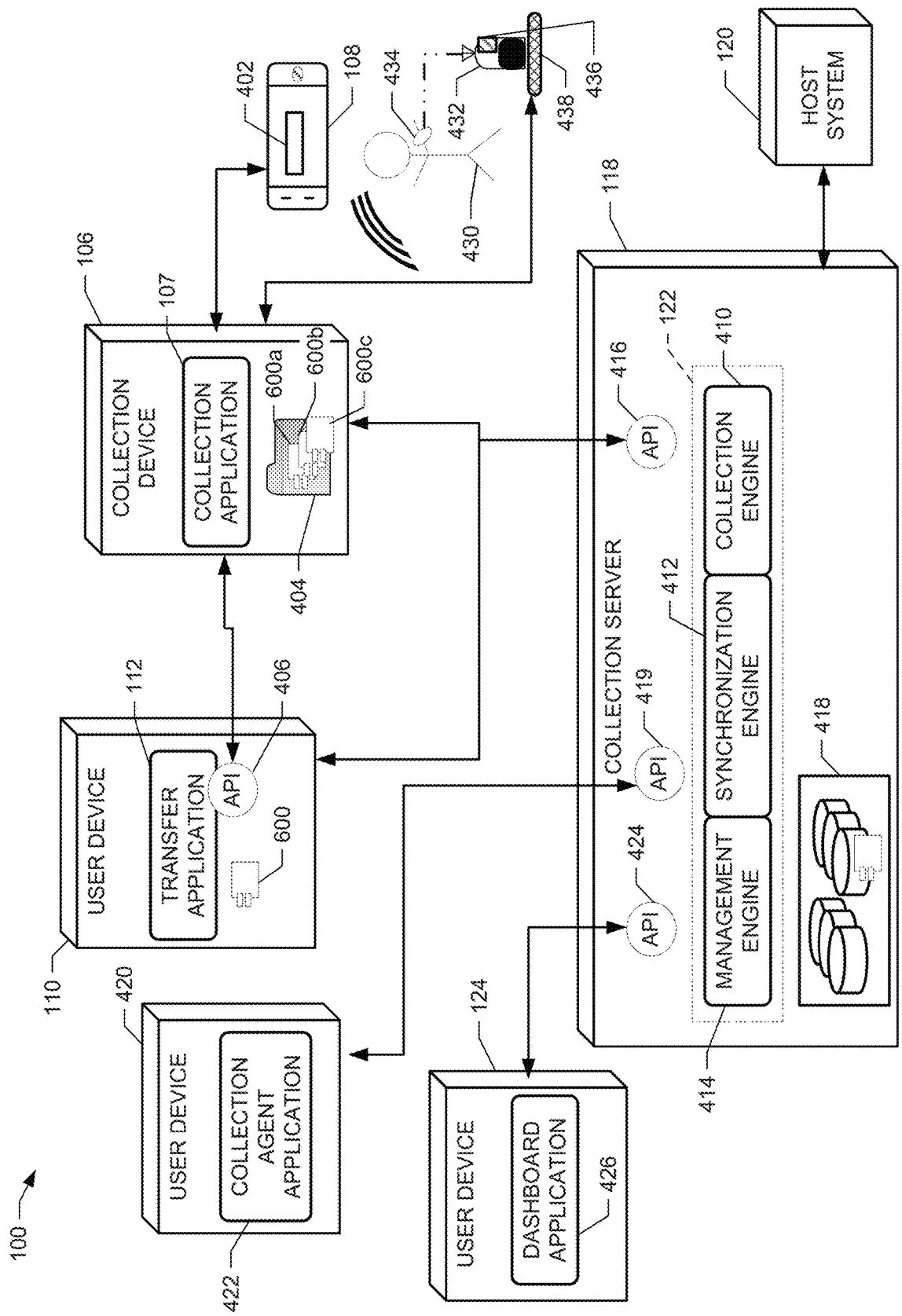
FIG. 4 shows a diagram of an application for use within the mobile file transfer environment of FIGS. 1 to 3, according to an example embodiment of the present disclosure.

FIG. 4 shows a diagram of an application for use within the mobile file transfer environment 100 of FIGS. 1 to 3, according to an example embodiment of the present disclosure. As discussed above, it is necessary to transfer blood donation information collected at the collection device 106 to the host system 120 via the collection server 118 for integration of blood collection data. The example shown in FIG. 4 provides a system for transferring sensitive blood donation information when a continuous network connection between a data reception site (e.g., the collection device 106) and the host system 120 is not available or reliable. As discussed below in conjunction with FIG. 4, this disclosed system uses the portability and multi-connection capabilities of smartphone phones (or similar devices) to bridge the gap in continuous network connectivity. At a first instant of time, a user device receives blood donation information from a collection device. The user device then moves to another location to establish a connection to a collection server for relaying the blood donation information.

I. Collection Device/Collection Application

Figure 5:
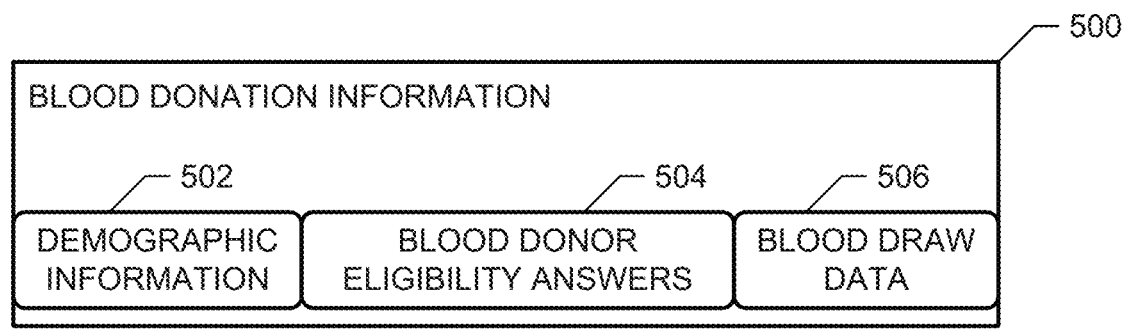
FIG. 5 shows a diagram of example blood donation information, according to an example embodiment of the present disclosure.

In the illustrated example of FIG. 4, the collection device 106 is communicatively coupled to one or more registration devices 108 via a local network and/or a direct connection. The collection device 106 is configured to operate the collection application 107 (e.g., a daemon application) for receiving blood donation information. Some of the blood donation information is received via a user interface of a registration application 402 operating on the registration device 108. Other of the blood donation information may be provided by a clinician or blood extraction device. FIG. 5 shows a example of blood donation information 500 that is collected by the collection application 107, according to an example embodiment of the present disclosure. The information 500 includes demographic information 502 and blood donor eligibility answers 504 provided by a user via the registration application 402. The demographic information 502 may include, for example, a name, an address, a donor identifier, a driver's license number, an age, a weight, a gender, a self-reported blood type, etc. The blood donor eligibility answers 504 include information provided by blood donors based on questions displayed via the registration application 402. The questions may prompt donors to provide information about past blood donations, travel history, sexual activity, smoking history, drinking history, drug history, health history, etc. For example, a question may ask a donor whether they traveled to a location known to have mosquitoes infected with the Zika virus.

The example blood donation information 500 also includes blood draw data 506, which may be provided by a clinician via the collection device 106, the registration device 108, and/or the user device 110. The blood draw data 506 may also be received from a blood pump or blood collection repository. The blood draw data 506 includes information specific to the donation of blood including, an amount of blood donated or processed. The blood draw data 506 may also include data from local testing performed during and/or after the donation. For example, blood processing machines may analyze a sample of the blood to test for certain diseases, cholesterol level, blood type, etc. The blood processing machines are configured to transmit the measurement data to the collection application 107 for storage as the blood draw data 506. In some embodiments, the blood draw data 506 may also include physiological information from physiological sensors (e.g., a heart rate sensor, a blood pressure sensor, a blood oxygen sensor, a weight sensor, a breathalyzer, etc.) connected to a blood donor.

Figure 6:
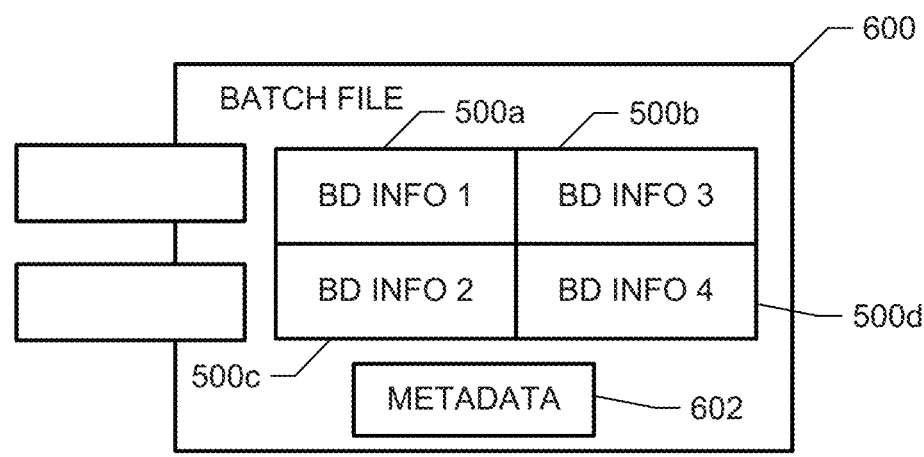
FIG. 6 shows a diagram of an example batch file, according to an example embodiment of the present disclosure.

The example collection application 107 is configured to store the blood donation information 500 within a batch file. FIG. 6 shows an example of a blood donation batch file 600, according to an example embodiment of the present disclosure. The batch file 600 includes blood donation information 500 related to different blood donors. The batch file 600 also includes metadata 602 configured to convey information related to a state of the file. The metadata 602 may include, for example, a number of blood donors for which blood donation information 500 is stored, a last update time of the batch file 600, a file size of the batch file 600, a file identifier of the batch file 600, and/or a creation date/time of the batch file 600. The metadata 602 may also include an identifier of the collection device 106, an identifier of the donation site 102, and/or an identifier of a user device 110. In some embodiments, the metadata 602 may include one or more flags indicative that the batch file 600 has been transferred to the collection server 118.

The example collection application 107 is configured to create and/or update the metadata 602 of the batch file 600 as new blood donation information 500 is received and/or when the status of the batch file 600 changes. For example, the collection application 107 stores a creation date/time corresponding to when the batch file 600 is created. The collection application 107 also determines an identifier of the collection device 106 and/or the collection site 102 and stores this identifier to the metadata 602. When new blood donation information 500, the collection application 107 stores the information to the batch file 600 and changes a last update time in the metadata 602. The collection application 107 may also determine a number of blood donors and/or file size and store this information to the metadata 602.

The example collection application 107 is configured to add blood donation information 500 to the batch file 600 as the information is received during a blood donation session. The collection application 107 may create a new batch file for each blood donation session and/or site. Alternatively, the collection application 107 may be configured to create a new batch file after a predetermined number of entries for blood donation information are created for a current batch file. For example, the collection application 107 may be configured to create a new batch file for every 100 blood donors.

The collection application 107 of FIG. 4 is configured to store the batch files 600 to a designated directory 404 within a file system of the collection device 106. Storage to the directory 404 publishes or makes the batch files available for discovery by devices (i.e., the user devices 110 and/or the collection server 118) that are configured with the name and/or location of the directory. In some instances, the user devices 110 and/or the collection server 118 may be configured with an address (e.g., a MAC or IP address) and/or identifier of the collection device 106 to facilitate or create a (secure) connection for batch file transfer.

In the illustrated example, the directory 404 includes three different batch files 500a, 500b, and 500c. In other embodiments, the directory 404 may include additional or fewer batch files. Further, the collection device 106 may include other directories that are hidden or unknown to the user devices 110 and/or the collection server 118. For example, after receiving confirmation that a batch file has been copied to the collection server 118, the example collection application 107 may transfer the copied batch from the directory 404 to a different directory. In these examples, the collection application 107 creates a new batch file after moving the transmitted batch file. In some instances, the collection application 107 may move the batch files to a different directory after the end of a blood donation session.

Alternatively, the collection application 107 may set a flag in the metadata of the batch file 600 at the directory 404 indicative that the batch file has been transferred. In these alternative embodiments, the collection application 107 may change the flag to unsent if the batch file is updated, modified, or otherwise written with new and/or updated blood donation information. In other words, any change to the batch file causes the collection application 107 to set the flag back to un-transmitted.

The example collection application 107 is also configured to graphically provide information related to the directory 404 and/or the stored batch files 600. For instance, the collection application 107 may display on the collection device 106 (or any device 110 or 118) that accesses the collection device 106) a status of the batch files 600 including at least some of the respective metadata. Such information may indicate which batch files 600 have been transferred (e.g., copied) to the collection server 118, which batch files 600 have been copied only to user devices 110, and/or which batch files 600 have not yet been transferred. The display of this information may be based on the flag metadata indicative of file transfer and/or a transfer date/time. The collection application 107 may also enable a user to view contents of the batch files 600.

In some instances, the collection application 107 may delete batch files 600 that have been transmitted to the collection server 118. For example, the collection application 107 may receive a message from the collection server 118 directly or via the user devices 110 indicative of the batch files that have been received. After receiving the message, the example collection application 107 is configured to delete, discard, or otherwise hide the batch files from transfer. The may include, for example changing a flag of the batch files to transferred. After a certain period, for example, at the end of a blood donation session, the collection application 107 may delete the flagged batch files. Alternatively, the collection application 107 may receive a prompt from a user of the collection device 106 indicative as to which batch files should be deleted.

The deletion of batch files may not occur unless a checksum value matches a checksum value of the batch file to be deleted. For instance, the message from the collection server 118 may include a checksum value of the transmitted batch file. Any difference with a checksum value of the corresponding batch file stored at the collection device 106 may be indicative that the batch file was not transmitted properly or incompletely. Instead of deleting the batch file, a difference in checksum values causes the collection application 107 to have the batch file remain available for transmission. The use of checksums provides file verification to ensure that identical copies of the batch files are made for each transmission.

In some instances, one or more of the applications 107, 112, and 122 may use checksum matching instead of or in conjunction with metadata to determine which batch files have already been transferred. For example, the management application 122 may determine that a checksum of a batch file differs between the copy stored at the collection server 118 and a copy stored at the user device 110. This may provide an indication that at least a portion of the batch file was improperly transmitted and/or the batch file has been updated. In response, the management application 122 may request a copy of the batch file at issue from the user device 110. In some instances, the management application 122 may request a user to verify which version of the batch file is correct or complete.

In some instances, the collection application 107 is configured to prevent batch files from deletion if they have not been transmitted to the collection server 118. For instance, after receiving a deletion indication from a user, the collection server 118 may determine if a transmission flag in the metadata 602 of the selected batch file is set to transferred. If the flag is set to transferred, the collection application 107 deletes the batch file from the designated directory 404. However, if the flag is not set (or the collection application 107 determines otherwise that the batch file has not been transferred to the collection sever 118), the collection application 107 disregards the delete instruction. The collection application 107 may also cause a warning to be displayed indicative that the selected batch file has not yet been transferred.

The example collection application 107 is also configured to ensure that the batch files are transmitted securely. For instance, the collection application 107 is configured to provide at least one layer of encryption for each batch file. In some instances, two layers of encryption (e.g., public-key or asymmetric cryptography) may be used to secure the sensitive blood donation information. The collection application 107 may encrypt only the blood donation information 500 or the metadata 502 in conjunction with the blood donation information 500.

The collection application 107 may also be configured (in connection with the transfer application 112 or the management application 122) to create a secure sockets layer ("SSL") and a virtual private network ("VPN") tunnel for transmission of the (encrypted) batch files. In instances where transmission is over a secure WLAN and/or a direct connection to the user devices (e.g., via NFC), the collection application 107 may transmit the encrypted batch files without a secure tunnel.

The example collection application 107 is configured to provide a discoverable network identifier for the collection device 106. In some instances, the collection application 107 may be configured to authenticate the user devices 110 prior to making the directory 404 available. For instance, the transfer application 112 may be configured to register the user device 110 with the collection application 107 of the collection device 106. Registration may occur by providing a user identifier, a unique client identifier, a device identifier, and/or a password. The collection application 107 maintains a list of registered devices so that only known and trusted user devices 110 have access to the blood donation information within the batch files.

II. User Device/Transfer Application

The example transfer application 112 operating within the user device 110 of FIG. 4 is configured to provide a bridge between the collection device 106 and the collection server 118 when a continuous network connection is not available. In the illustrated embodiment, the transfer application 112 includes an application program interface ("API") 406 configured to acquire batch files from the collection device 106. The API 406 may include a Representational State Transfer ("REST") API and/or a JavaScript Object Notation ("JSON") API, for example. After receiving the batch files 500, the transfer application 112 is configured to detect a connection to the collection server 118 and accordingly transmit the stored batch files. In some examples, the user device 110 may not include a public key that prevents a user from accessing data within the batch files. Such a configuration ensures that the batch files may only be encrypted and decrypted for reading at the source and destination.

In the illustrated embodiment, the transfer application 112 is configured to detect that the user device 110 is communicatively coupled to the collection device 106. For instance, the transfer application 112 may determine the collection device 106 is on a same LAN or WLAN as the user device 110. The transfer application 112 may use a programmed address (e.g., a MAC or IP address) and/or an identifier of the collection device 106 to transmit one or more ping or poll messages for creating a connection with the collection device 106. Alternatively, the transfer application 112 may determine that the user device 110 is directly connected to the collection device 106 via a direct secure connection such as Bluetooth® or NFC. In some instances, the connection may not occur until after the user device 110 is authenticated by the collection device 106.

After determining the collection device 106 is connected, the transfer application 112, using the API 406 at periodic intervals (e.g., 5 minutes, 10 minutes, 30 minutes, etc.), determines if there are any updated and/or new batch files at the designated directory 404. To determine if there are any new and/or updated batch files, the transfer application 112, via the API 406, is configured to request metadata 602 of batch files stored at the designated directory 404. The transfer application 112 discards the metadata 602 that includes a set transfer flag (indicative that the batch file was already transmitted to the collection server 118). In alternative embodiments, the collection device 106 may only transmit the metadata 602 if the flag is not set. The transfer application 112 then compares the metadata to the metadata of batch files already stored on the user device 110 or metadata associated with previously deleted batch files. Comparing may include, for example, matching file identifiers in conjunction with file last update times and/or number of blood donors and/or matching checksums of batch files. For a match to occur, substantially all of the metadata should match. However, metadata with different last updated times, file sizes, number of blood donors, etc. are indicative that a batch file with a matching identifier may have been updated.

After determining which batch files have been updated and/or new, the example transfer application 112 transmits to the collection application 107 a request for the identified batch files. The transfer application 112, via the API 406, accordingly acquires a copy of the requested batch files. The transfer application 112 stores the received batch files to a memory of the user device 110. Additionally, the transfer application 112 overwrites (e.g., replaces the old batch file with the newly received batch file) batch files that have been updated or modified with the more recent version. In alternative embodiments, the transfer application 112 maintains the different versions of the same batch file. The transfer application 112 may also perform a checksum of the received batch files and transmit the checksum for each file to the collection device 106 to provide file transmission verification.

The example transfer application 112 may be configured to update metadata for newly received copies of batch files. For example, the transfer application 112 may add a user identifier of the user device 110 and/or a time/date the batch file was received at the user device 110 to the metadata 602. The user identifier may include, for example, a natural language identifier provided by a user (e.g., "Jack's Phone").

The transfer application 112 is configured to maintain the encrypted batch files 600 (e.g., the copy of the batch files at the collection device 106) for eventual transmission to the collection server 118. This may include storing the batch files to a preassigned directory (specified in the transfer application 112) that may be restricted from access by a user of the user device 110. The use of encryption and/or a hidden directory prevents users of the user devices 110 and/or other applications on the user devices 110 from being able to read the blood donation information. In some instances, the transfer application 112 may periodically check whether the user device 110 is connected to the network 116. Upon detecting a connection (and/or determining there exists at least one batch file for transmission), the transfer application 112 may transmit a notification message to the collection server 118 indicative that the transfer application 112 is online and available. Alternatively, the transfer application 112 may receive a ping or poll message from the collection server 118 determining which user devices 110 are connected.

In addition to detecting the connection, the transfer application 112 may operate in connection with the management application 122 to authenticate and/or provide information that is indicative of being a registered device. The transfer application 112 may accept and/or create a VPN tunnel and/or SSL to the collection server 118 for the sharing of metadata and transfer of requested batch files. In some instances, the VPN tunnel and/or SSL may not occur unless the collection server 118 is to receive at least one batch file. For instance, after connecting to the transfer application 112, the collection server 118 requests the metadata 602 for the batch files stored on the user device 110. The transfer application 112 is configured to provide the metadata 602 for batch files available for transmission. The transfer application 112 then receives a message from the collection server indicative of any batch files to transfer. At this point, the transfer application 112 may create or open a secure connection to the collection server 118 for the transfer of the requested files. The transfer application 112 then transfers the batch files that are new or updated to the collection server 112.

The transfer application 112 may, additionally or alternatively, receive checksum values from the collection server 118 associated with transferred batch files. The transfer application 112 may transmit a re-transmit message to the collection server 118 if the received checksum value does not match the value determined from the locally stored copy of the batch file. Upon receiving the re-transmit message, the collection server 118 discards the received batch file and starts procedures with the transfer application 112 to acquire a new copy of the batch file. If the checksum values match, the transfer application 112 may set the transfer flag within the metadata 602. As discussed before, setting the transfer flag helps reduce the possibility that the flagged batch file is made available to the collection server 118 at subsequent times. Setting the flag also prevents the user device 110 from receiving the same batch file from the collection device 106.

Alternatively when no flags are used, the transfer application 112 is configured to retain the batch file, or at least the metadata of the batch file as being indicative that the file has been transferred. In some instances, the encrypted contents of the batch file may be deleted while the metadata is maintained to ensure duplicate files are not transmitted to the collection server 118.

The transfer application 112 is also configured to provide a graphical display within a user interface of the user device 110 indicative of a status of locally stored batch files 600. The transfer application 112 may be configured to display, for example, a number of batch files that have been transferred and/or a number of batch files that are on the user device 110 but have not yet been transferred to the collection server 118. Additionally or alternatively, the transfer application 112 may provide a file name and/or identifier of local copies of batch files as well as reception time/date, transmission time/date, and/or an indication whether the batch file was transferred to the collection server 118. Further, the transfer application 112 may be configured to display an identifier of the collection device 106 and/or collection site 102 from which the batch file originated. The transfer application 112 may also provide a graphical indication as to whether a connection to the collection device 106 and/or the collection server 118 exists (or is available).

III. Collection Server/Management Application

The example collection server 118 is configured to acquire batch files 600 from the user devices 110 and/or the collection devices 106. The collection server 118 may be implemented on, for example, a Rackspace® host cloud provider. FIG. 4 shows that the management application 122 operating on the collection server 118 includes a collection engine 410, a synchronization engine 412, and a management engine 414. However, it should be appreciated that the management application 122 may be configured differently in other embodiments.

The collection engine 410 includes an API 416 configured to acquire batch files 600 from the user devices 110 and/or the collection devices 106. In some embodiments, the collection engine 410 uses a device list to send periodic ping or poll messages to determine which user devices 110 and/or collection devices 106 are connected to the network 116. The device list may include, for example, IP addresses, MAC addresses, phone numbers, etc. related to the user devices 110 and/or the collection devices 106. The collection engine 410 receives an error response if a poll and/or ping message is undeliverable, indicative that the user device 110 and/or the collection device 106 is not connected to the network 116. In other instances, the collection engine 410 may determine after a predetermined time during which no response is received that the user device 110 and/or the collection device 106 is not connected to the network 116. The collection engine 410 determines a user device 110 and/or collection device 106 is connected responsive to receiving a response message. In some instances, the collection engine 410 may maintain a list of which devices 106 and 110 are currently connected to the network 116. Contents of the list may be made available on a dashboard or other user interface.

In other embodiments, the collection engine 410 may not send poll or ping messages. Instead, the collection engine 410 may be configured to wait for a message from a user device 110 and/or collection device 106 indicative that the device is connected to the network 116. In either of these embodiments, the collection engine 410 may authenticate the user device 110 and/or the collection device 106 to ensure the device is a registered known device.

After detecting connected devices 106 and 110, the collection engine 410 is configured to determine which batch files are to be transmitted. In other words, the collection engine 410 is configured to pull batch files from visible devices 106 and 110. To determine which batch files are to be transmitted, the collection engine 410, via the API 416, is configured to read or otherwise obtain the metadata 602 of the batch files 600 on the connected devices 106 and 110. In some instances, the collection engine 410 is configured to read or obtain batch files with metadata 602 having a transmission flag that is not set. In other examples, the collection engine 410 may receive metadata 602 of all batch files locally stored at the devices 106 and 110. In these other examples, the collection engine 410 filters the metadata that have set transmission flags.

After receiving the metadata 602, the collection engine 410 in conjunction with the synchronization engine 412 is configured to compare the received metadata to metadata of already received batch files located, for example, in database 418. The collection engine 410 determines that batch files with matching metadata do not need to be transmitted. The collection engine 410, via the API 416, may transmit a message, indicative that the transmission flag should be set, to the device 106 and/or 110 that previously provided the matching metadata. If the batch file is located on the user device 110 (as opposed to the collection device 106), the transfer application 112 may delete the blood donation information and retain the metadata for a predetermined time period.

In instances where the metadata does not match, the collection engine 410, via the API 416 is configured to read or otherwise acquire the respective batch files from the corresponding devices 106 and 110. The collection engine 410 stores the batch files to the database 418. The collection engine 410 may also calculate a checksum of the transmitted batch file and transmit a transmission acknowledgement message that includes the checksum to the appropriate device 106 and 110. The acknowledgement message may cause the device 106 and/or 110 to set the transmission flag in the metadata of the local copy of the transmitted batch file (if the checksum matches) to prevent re-transmission at a later time. The acknowledgement message may also cause the transfer application 112 to delete contents of the transmitted batch file.

In some instances, the synchronization engine 412 determines that more than one of the devices 106 and 110 has a copy of the same batch file. In these instances, the collection engine 410 may give priority to the collection device 106 and/or the user device 110 with the most reliable connection, which may be determined based on a timing of a response to a previously transmitted ping/poll message. The collection engine 410 is configured to acquire the batch file from one of the devices 106 and 110. If the batch file is not properly received from the first device, the collection engine 410 may attempts to acquire the batch file from another device. After the batch file is successfully transmitted to the collection server 118, the collection engine 410 transmits messages to the other devices 106 and/or 110 indicative that the batch file has already been received, thereby causing the transmission flag to be set in the metadata (and/or the contents of the file to be deleted).

In some instances, portions of a batch file may be distributed to more than one device. In these instances, the collection engine 410 uses the metadata of each file portion to determine how the batch file is to be reconstructed from the two (or more) different devices 106 and 110. Such a configuration may be used when batch files are especially large and have a large transmission time from any one device 106 and/or 110.

The collection engine 410 may create a secure VPN tunnel and/or SSL to facilitate the transmission of the batch file and/or the metadata. In some embodiments, the collection engine 410 creates a secure VPN tunnel or SSL to each connecting user device 110 and/or collection device 106. In other examples, the collection engine 410 is configured to create the VPN tunnel and/or SSL to only a device 106 or 110 when a batch file transfer is to occur. Such a configuration only creates a secure path only when sensitive data is transmitted, which does not include the metadata. In yet other configurations, the collection engine 410 is configured to use a file transfer protocol ("FTP") to acquire the batch files from the devices 106 and/or 110.

The example synchronization engine 412 of the collection server 118 is configured to ensure that only one copy of a batch file is received. For example, the collection engine 410 stores a copy of a received batch file to the database 418. The synchronization engine 412 is configured to perform the comparison of received metadata to metadata of already stored batch files. For instance, the synchronization engine 412 may compare file identifier metadata and/or date created metadata to determine whether the metadata matches. The synchronization engine 412 provides a result of the comparison to the collection engine 410. As discussed above, metadata that matches is indicative that a copy of the batch file is already stored in the database 418. In instances where there is a file identifier match but the date/time of the last update differs, the synchronization engine 412 is configured to replace the batch file stored in the database 418 with a newer version of the batch file received from the device 106 and/or 110. In other embodiments, the synchronization engine 412 may store a copy of both versions and flag the files for further inspection and/or analysis.

The example synchronization engine 412 includes an API 419 configured to enable a user device 420 operating a collection agent application 422 to read and/or modify batch files stored in the database 418. The user device 410 may be in possession of a manager or administrator tasked with maintaining the integrity of the batch files. The collection agent application 422 is configured to use the API 419 to access the database 418 to read the metadata of the batch files. The collection agent application 422 is configured to graphically show the batch files and enable selection causing the synchronization engine 412 to provide a copy of the selected batch file. The collection agent application 422 may also include a decryption key to enable the blood donation information to be decrypted for viewing and/or modification. In some instances, the collection agent application 422 may display an alert indicative that at least one batch file needs attention (in a case when there are two versions of the same batch file). A user of the user device 410 may then determine which batch file is to be discarded.

The example management engine 414 is configured as a web application configured to provide a graphical representation of the batch file collection process. The management engine 414 includes an API 424 that enables a dashboard application 426 on management user device 124 to view a status of transferred batch files. The API 424 is configured to process requests for status data, which is transmitted to the management engine 414. The example management engine 414 reads the contents of metadata of the batch files and transmits this information to the dashboard application 426, which is configured to show the contents of the metadata in a graphical representation.

FIG. 7 shows a diagram of an example graphical representation 700 of batch file metadata displayed within a user interface 702 provided by the dashboard application 426, according to an example embodiment of the present disclosure. The user interface 702 is organized by collection device 106 (e.g., Laptop A, Laptop B, Laptop C). Further, for each collection device 106, the user interface 702 includes at least some metadata for each batch file including a batch file name, a location from which the file was collected, a size of the file, a time stamp when the file was received at the collection server 118 and/or the user device 110, a time the file was created and/or last updated, and/or an identifier of a user device used to transfer the file. It should be appreciated that the user interface 702 may include additional or fewer fields in other embodiments. For instance, the user interface 702 may include information indicative of a number of times a batch file was overwritten and/or updated. The user interface 702 provided by the dashboard application 426 enables a user to view which files are at the collection server 118 before transmission to the host system 120. In some instances, the user interface 702 in connection with the dashboard application 426 may include features for instructing the collection server 118 to transmit the batch files to the host system 120 and/or to modify, edit, and/or delete batch files.

In addition to providing a graphical management interface, the example management engine 414 may also be configured to decrypt the batch files stored in the database 418. For instance, the management engine 414 may decrypt the batch files if a secure VPN tunnel and/or SSL exists with the host system and/or the collection server 118 is within the same LAN as the host system 120. Alternatively, the management engine 414 may leave the batch files encrypted if a more unsecure file transfer method is used, such as FTP. In some instances, the management engine 414 may decrypt the batch files, aggregate or package the batch files for transmission in a single package or large file, then encrypt the single file for transmission.

IV. Push Embodiment

The above-described file transfer system uses a pull configuration. However, in some embodiments, the collection application 107, the transfer application 112, and/or the management application 122 may use a push configuration. For example, the collection application 107 at the collection device 106 determines which user devices 110 and/or collection server 118 is connected. Upon making a connection, the collection application 107 pushes or transmits all newly created and/or updated batch files since the last transmission. The receiving transfer application 112 is configured to read the metadata of the incoming batch files to determine which ones are new and/or updated with respect to the user device 110. Any batch files with matching metadata may be discarded by the transfer application 112.

The transfer application 112 then pushes the locally stored batch files to the collection server 118 upon making a secure connection. The management application 122 is configured to determine which metadata of the received files matches metadata of batch files already stored to the database 418. The management application 122 stores batch files with non-matching metadata to the database 418 and discards the batch files that have matching metadata.

In yet another embodiment, the collection application 107 is configured to push the metadata to the transfer application 112. The transfer application 112 determines which metadata does not match metadata of locally stored batch files and transmits an identifier of the non-matching metadata. The collection application 107 may then transmit the batch files associated with the non-matching metadata. The example transfer application 112 may perform a similar method with the management application 122 where only the metadata of the stored batch files is initially pushed or transmitted.

In yet a further embodiment, the collection application 107 is configured to check a published directory in the user device 110 that includes the batch files. The collection application 107 determines which batch files have already been received at the user device 110 by comparing metadata. The collection application accordingly only transmits the new and/or updated batch files. The transfer application 112 may operate in the same manner with respect to the collection server 118. In this instance, the transfer application 112 reads the metadata of the batch files stored within the database 418 (or a file that lists the metadata of the stored batch files) to determine which locally stored batch files are new and/or updated. The transfer application 112 may only open a secure connect with the collection server 118 when a batch file is to be transmitted. Alternatively, the transfer application 112 creates a secure connection before reading the contents of the database 418 (or metadata file).

V. Blood Measurement Embodiment

In some embodiments, the mobile file transfer environment 100 of FIGS. 1 to 4 may be used in connection with just-in-time inventory tracking of blood supplies. Traditionally, donated blood is stored in a blood bank until it is needed. This typically means preserving the blood (i.e., whole blood) for long term storage at a reduced temperature between 1° and 6° centigrade ("C"). However, to preserve platelets, the blood cannot be stored below 22 to 24° C., which means the blood cannot be stored for long periods of time before deterioration occurs. The example mobile file transfer environment 100 may be used to route donated blood to an identified recipient without first being stored in a blood bank.

FIG. 4 shows that during blood donation, a donor 430 is fluidly connected to one or more blood bags 432. An intravenous ("IV") needle is placed into the donor to draw blood, which is routed via an IV tube to the blood bags 432. In some instances, one or more sensors 434 may be placed in-line with the IV tube and/or the IV needle to detect one or more properties of the blood (e.g., blood draw data 506 of FIG. 5). The sensors 434 may include, for example, micro-system on a chip sensors. The sensors 434 may also be configured to acquire a blood sample for further processing by a blood analyzer. In some instances, the sensors 434 may include a (disposable) cartridge or cassette that is insertable into a blood analyzer.

Collectively, the sensors 434 may measure (or facilitate the measurement of), for example, a blood type, a presence (or concentration) of alcohol, drugs, or other chemicals, platelet count, cholesterol, sodium level, potassium level, diseases, etc. The sensors 434 may also measure an amount of blood drawn. The data collected by the sensors 434 (or determined by a blood analyzer) is transmitted to the collection device 106 for inclusion within the blood donation information 500. FIG. 4 shows that the sensor 434 may wirelessly transmit the blood draw data.

In addition to the sensors 434, the blood bag 432 may include one or more smart sensors 436 configured to determine one or more properties of the donor's blood. In some instances, the smart sensors 436 may include an RFID chip or NFC chip that may be read by a reader connected to the collection device 106 and/or the registration device 402. For example, the blood bag sensor 436 may include a micro or nano system-on-a chip configured to determine blood type, sodium levels, and potassium levels. The measurement data is stored in a local memory within the sensor 436, which is read by a reader. In some instances, the sensor 436 may be programmed with an identifier of the donor 430 and/or an identifier of the respective blood donation information 500. The identifier enables the blood bag 432 to be associated with the blood donation information 500 at the host system 120.

The example of FIG. 4 also includes a weight sensor 438 configured to measure a weight of the blood bag 432. The weight sensor 438 may be used to determine an amount of blood donated. As illustrated, the weight sensor 438 is communicatively coupled to the collection device 106.

In a just-in-time embodiment, the blood draw data 506 determined by the sensors 434, 436, and/or 438 is received in the collection device 106 and aggregated with the other blood donation information 500 associated with the same blood donor 430. The blood donation information 500 is stored in a batch file 600, which is transmitted to the collection server 118 directly or via the user device 110. The user of the user devices 110 enables the blood donation information 500 to be received at the collection server 118 relatively quickly by bridging any gaps in a continuous network connection between the collection device 106 and the collection server 118. The collection server 118 communicates with the host system 120, which may include a list of patients that are in need of donated blood. The list may include a blood type and other desired characteristics of the blood. The host system 120 is configured to use the blood donation information 500 to determine a match to a particular recipient.

If the host system 120 makes a match, the host system 120 may transmit a message to the collection device 106 indicative of a destination for the corresponding donated blood. To enable the message to be received at the collection device 106, the host system 120 transmits the message via the network 116 to the collection server 118, which transmits the message to connected user devices 110 associated with the collection device 106. The collection server 118 may determine the user devices 110 associated with the collection device 106 based on metadata of received batch files that are indicative of the user device(s) 110 and collection device 106 that originated the batch files or facilitated the transfer of the batch files. The user devices 110 receive the message, and some time later travel back in proximity to the collection device 106. Once in proximity of the local network or connection, the user devices 110 relay the message to the collection device 106, which then displays the message as an alert to a user. Responsive to seeing the alert, the user may locate the bags 432 of donated blood identified in the message and arrange for the immediate transfer of these bags to the intended recipient. In some embodiments, additionally needed blood tests may be performed at the recipient site or in parallel with blood transportation to ensure the blood is safe for transfusion or other uses.

It should be appreciated that the just-in-time process may be used to route blood bags in other locations. For instance, the host system 120 may track locations of blood bags and determine destination for routing messages based on the tracked location. Specifically, the host system 120 may determine whether a blood bag is in transit from a donation site, in temporary storage awaiting blood testing, or located within a blood bank. In other embodiments, the host system 120 may provide a list of needed blood and locations to the collection device 106, which is configured to make the comparison to blood donation information 500 as it is received. It should also be appreciated that the mobile file transfer environment 100 of FIGS. 1 to 4 may be used in connection with organ and tissue transplants instead of blood donation.

VI. Biometric Health Assessment Embodiment

The example mobile file transfer environment 100 of FIGS. 1 to 4 may be used in connection with the collection of biometric health screening information. Many workplaces, schools, churches, and community events sponsor free (or discounted) heath screenings. Typically, a health screening includes a provider tasked with taking a blood sample, performing a weight/height/waist measurement, and taking a blood pressure reading. The blood sample is processed in a blood analyzer to determine, for example, total cholesterol, HDL and LDL cholesterol, non-HDL cholesterol, triglycerides, and glucose. Further, other physiological sensors may be used to determine physiological parameters including heart rate, blood oxygen level, lung capacity, etc. Similar to blood donations, these events typically occur in building locations with limited or no network connectivity.

In these embodiments, the collection device 106 is configured to acquire health assessment information, which may be input by a clinician or an individual undergoing a screening. The information may also be received via a WLAN or direct connection to a blood analyzer, scale, and/or blood pressure machine. Similar to the examples discussed above in connection with FIGS. 1 to 4, the collection device 106 transmits batch files of health assessment information to user devices 110 when a connection to the network 116 is not available. The user devices 110 then transfer the batch files to the collection server 118, which provides the files to the host system 120. The example host system 120 may process the health assessment information to make it viewable to the respective individuals via an online health portal. The host system 120 may also transmit the health assessment information for each individual to a medical record or to a medial provider. Such a configuration enables sensitive medical data to be transmitted securely to a central location without having to physically move the collection devices to a network connection or physically transport the data.

Mobile File Transfer Example Procedures

Figure 8:
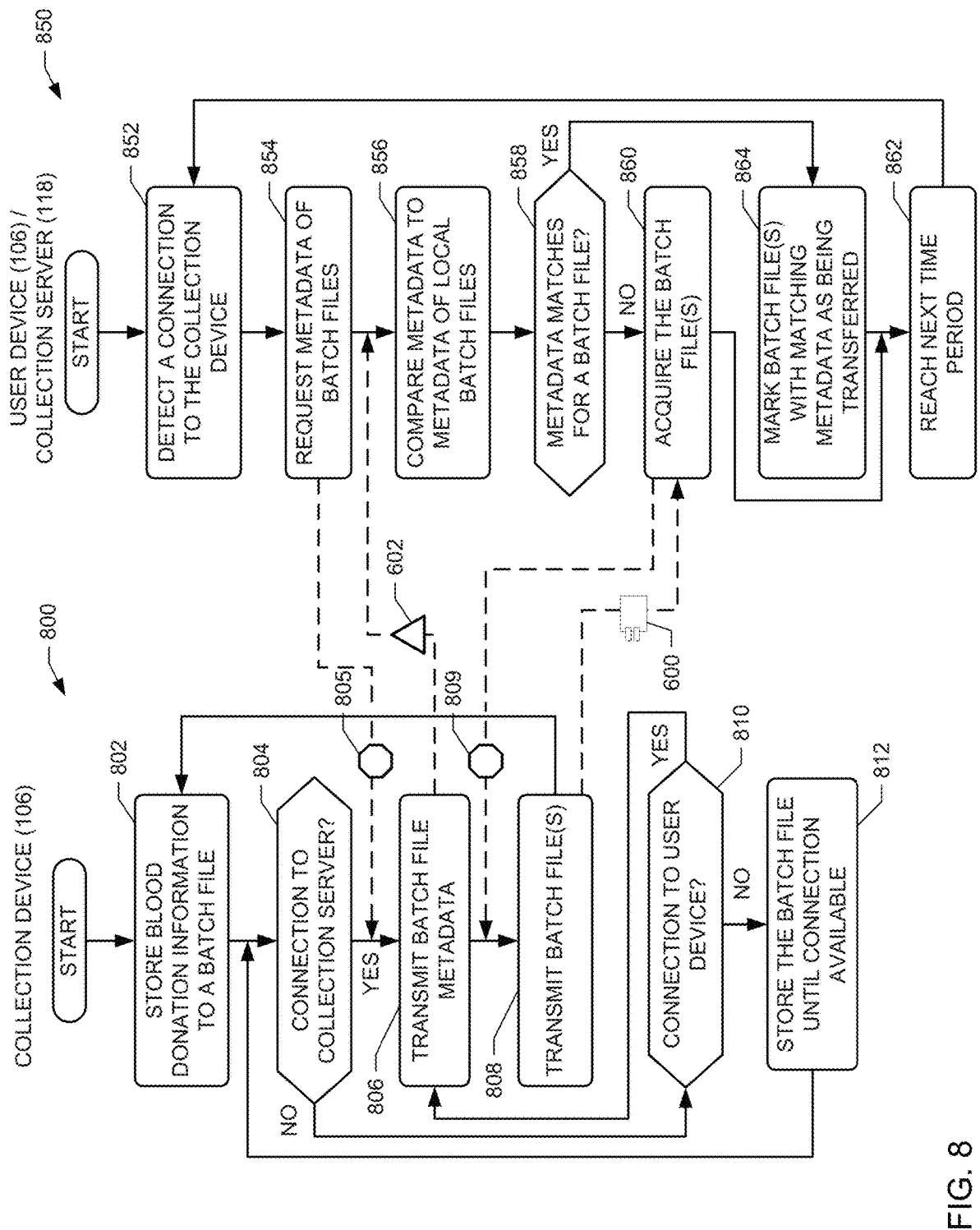
FIGS. 8 and 9 illustrate flow diagrams showing example procedures to transfer batch files from a collection device to a collection server, according to example embodiments of the present disclosure.
Figure 9:
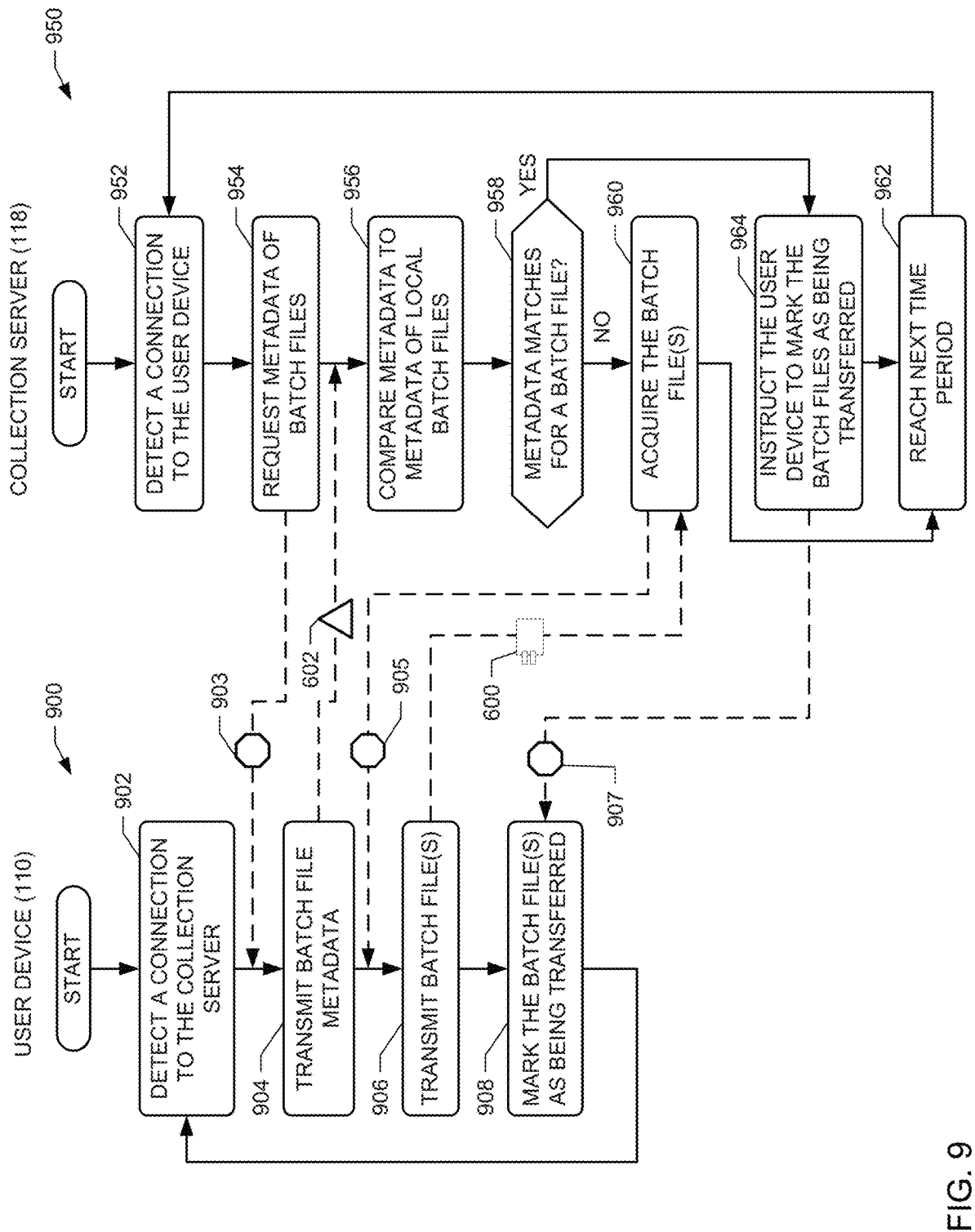

FIGS. 8 and 9 illustrate flow diagrams showing example procedures 800, 850, 900, and 950 to transfer batch files 600 within the mobile file transfer environment 100 of FIGS. 1 to 4, according to example embodiments of the present disclosure. Although the procedures 800, 850, 900, and 950 are described with reference to the flow diagrams illustrated in FIGS. 8 and 9, it should be appreciated that many other methods of performing the steps associated with the procedures 800, 850, 900, and 950 may be used. For example, the order of many of the blocks may be changed, certain blocks may be combined with other blocks, and many of the blocks described are optional. For example, the procedures 800, 850, 900, and 950 may not set a transmission flag or delete batch files upon transmission to the collection server 118. In another example, the procedures 800, 850, 900, and 950 may include performing a checksum comparison to verify the batch files were copied correctly and/or authenticating or registering user devices 110 with the collection device 106 and/or the collection server 118. The actions described in procedures 800, 850, 900, and 950 may be performed among multiple devices including, for example the collection device 106, the user devices 110, and/or the collection server 118.

Procedures 800 and 850 relate to the transfer of batch files from the collection device 106 to the user device 110 or the collection server 118. The example procedure 800 of FIG. 8 begins when the collection application 107 of the collection device 106 receives and stores blood donation information 500 to a batch file 600 (block 802). As discussed above, the blood donation information 500 may be received from registration devices 404 and/or sensors 434, 436 and/or 438. The collection device 106 determines whether a network connection to the collection server 118 exists (block 804). If a connection exists (as shown in FIG. 3), the collection device 106 receives a request message 805 from the collection server 118 to acquire metadata of locally stored batch files located at a designated directory (block 806). The transfer application 107 provides the collection server 118 access to the designated directory to read the metadata 602, which may be provided to the collection server 118 in one or more messages.

After comparing the read metadata to metadata of copies of batch files already stored at the collection server 118, the collection device 106 receives a batch file request message 809 indicative of batch files to be transmitted. The transfer application 107 accordingly transmits the requested batch files 600 to the collection server (block 808). As discussed above, transmitting the batch files 600 includes enabling the collection server 118 to read the designated directory to make a copy of the desired batch files. In some embodiments, the collection device 106 may not receive a message if the collection server 118 already has a copy of all of the batch files located at the collection device 106. Alternatively, the request message 809 may indicate that no batch files are to be transmitted.

While (and after) interacting the collection server 118, the collection device 802 continues to acquire blood donation information (block 802). If the connection to the collection server becomes disconnected (or never existed) (block 804), the collection device 106 determines if a connection to one or more user devices 110 are available (block 810). In some embodiments, the collection device 106 may still connect to user devices 110 even if a connection to the collection server 118 exists. If no connection exists to a user device 110, the collection device 106 stores batch files until a connection is established to at least one of the user devices 110 and/or the collection server 118 (block 812). However, if a connection to at least one user device 110 is established, the collection device 106 is configured to provide access to metadata and batch files for each connected user device 110 in the same manner as the collection server 118 discussed above (blocks 806 and 808). For instance, each connected user device 110 locally uses metadata to determine which batch files on the collection device 106 are new and/or updated. Each user device 110 then makes a local copy of each new and/or updated batch file. The example procedure 800 may continue until the blood donation session ends or the collection device 106 is deactivated.

The example procedure 850 of FIG. 8 may be performed by the user device 110 and/or the collection server 118 to acquire new and/or updated batch files. The procedure 850 begins when the user device 110 and/or the collection server 118 detects a connection to the collection device 106 (block 852). After detecting the connection, the user device 110 and/or the collection server 118 transmits a request message 805 to read, acquire, access, or otherwise obtain metadata of batch files stored at a designed directory of the collection device (block 854). After receiving the metadata 602, the user device 110 and/or the collection server 118 compares the received metadata to metadata of locally stored batch files to determine which batch files are new and/or updated (block 856).

The user device 110 and/or the collection server 118 determine if the received metadata for all of the batch files matches the metadata for all of the locally stored batch files (block 858). The user device 110 and/or the collection server 118 transmits a batch file request message 809 indicative of the batch files associated with un-matched metadata (block 860). The user device 110 and/or the collection server 118 then receives the requested batch files 600 associated with un-matched metadata (block 860). In some embodiments, the message 809 includes messages transmitted by the user device 110 and/or the collection server 118 to read and copy the batch files at the collection device 106 that are associated with un-matched metadata. After a predetermined time period (e.g., 5 minutes, 15 minutes, 30 minutes, etc.), the user device 110 and/or the collection server 118 determines whether the connection to the collection device 106 still exists and performs another read of the designated directory to determine new and/or updated batch files (blocks 862 and 852 to 858).

Returning to block 858, the user device 110 and/or the collection server 118 may determine that all of the received metadata matches metadata of locally stored copies of batch files. In these instances, the user device 110 and/or the collection server 118 may mark or otherwise indicate that the local copies of the batch files have already been received from the collection device 106 (block 864). Alternatively, the presence of the copies of the batch files themselves may be indicative of the pervious transfer, thereby making method performed in block 864 unnecessary. Regardless, after a predetermined time period, the user device 110 and/or the collection server 118 determines whether the connection to the collection device 106 still exists and performs another read of the designated directory to determine new and/or updated batch files (blocks 862 and 852 to 858).

Procedures 900 and 950 relate to the transfer of batch files from the user device 110 to the collection server 118. Procedure 900 begins when the user device 110 detects a connection to the collection server (block 902). In some instances, the user device 110 has to move to a location remote from the collection device 106 to acquire the network (e.g., wireless) connection to the Internet. In other instances, the user device 110 may be connected to a cellular network while being connected to the collection device 106 via a local network and/or a direct connection.

The user device 110 may detect the connection to the network 116, then establish a connection with the collection server 118. Alternatively, the collection server 118 may transmit one or more poll or ping messages to determine when the user device 110 is connected to the network 116. The collection server 118 may then establish a connection through the network 116 with the user device 110. After detecting the connection, the user device 110 receives a request message 903 from the collection server 118 to view metadata of locally stored batch files. In response to the request message 903, the user device 110 transmits the metadata 602 of the batch files in one or more messages (block 904). Transmitting the metadata 602 may also include enabling the collection server 118 to read the metadata of the batch files stored on the user device 110.

After the collection server 118 compares metadata, the user device 110 receives a batch file request message 905 indicative of the batch files to be copied to the collection server 118. The user device 110 accordingly transmits the requested batch files 600 to the collection server 118 in one or more messages (block 906). Transmitting the batch files 600 may include enabling the collection server 118 to read and store a copy of the new and/or updated batch files located on the user device 110. In some embodiments, the user device 110 may receive an acknowledgement message 907 from the collection server 118 indicative that the batch files 600 were transmitted. The acknowledgement message 907 may include a checksum value for each transferred batch file. The user device 110 may compare the received checksum to a checksum value of the locally stored batch files to verify the file transmission was successful. In other instances, the collection server 118 may re-read the batch files on the user device 106 to determine a checksum value and compare the determined value to a checksum value calculated from a copy of the batch file newly stored at the collection server 118.

The user device 110 may then (in some instances) mark the locally stored batch files as being transferred (block 908). Alternatively, the user device 110 may not change the metadata on the transferred batch files. In yet alternative embodiments, the user device 110 may delete or otherwise make the copied batch files unavailable for subsequent access. Regardless, the procedure 900 returns to blocks 902 to 906 when the collection server 118 checks for new and/or updated batch files on the user device 110 at a predetermined subsequent time.

The procedure 950 begins when the collection server 118 detects a connection to the user device 110 (block 952). After detecting the connection, the collection server 118 transmits a request message 903 to read, acquire, access, or otherwise obtain metadata of batch files stored at the user device 110 (block 954). The batch files may be located at a directory related to transfer application 112 or made known to the management application 122. After receiving the metadata 602, the collection server 118 compares the received metadata to metadata of locally stored batch files to determine which (if any) batch files on the user device 110 are new and/or updated (block 956).

The collection server 118 determines if the received metadata for all of the batch files matches the metadata for all of the locally stored batch files (block 958). The collection server 118 transmits a batch file request message 905 indicative of the batch files associated with un-matched metadata (block 960). The collection server 118 then receives the requested batch files 600 associated with un-matched metadata (block 960). In some embodiments, the message 905 includes requests transmitted by the collection server 118 to read and copy the batch files at the user device 110 that are associated with un-matched metadata. After a predetermined time period (e.g., 5 minutes, 15 minutes, 30 minutes, etc.), the collection server 118 determines whether the connection to the user device 110 still exists and performs another read of the designated directory to determine new and/or updated batch files (blocks 962 and 952 to 958).

Returning to block 958, the collection server 118 may determine that all of the received metadata matches metadata of locally stored copies of batch files. In these instances, the collection server 118 may mark or otherwise indicate that the local copies of the batch files have already been received from the user device 110 (block 964). Alternatively, the presence of the copies of the batch files themselves may be indicative of the pervious transfer, thereby making method performed in block 964 unnecessary. Regardless, after the predetermined time period, the collection server 118 determines whether the connection to the user device 110 still exists and performs another read of the designated directory to determine new and/or updated batch files (blocks 962 and 952 to 958).

CONCLUSION

It will be appreciated that all of the disclosed methods and procedures described herein can be implemented using one or more computer programs or components. These components may be provided as a series of computer instructions on any computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A collection server having non-tangible instructions stored in a memory, that are configured when executed by the collection server, to cause the collection server to: determine, first, whether communication is possible with a local collection device that is configured to store blood donation information within a batch file having metadata related to (i) the blood donation information and (ii) a status of the batch file; responsive to determining that communication is not possible with the local collection device, determine, next, whether communication is possible with a remotely located first user device that is configured to store a copy of the batch file at the local collection device; after determining that communication is not possible with the local collection device and then determining that communication is possible with the remotely located first user device, acquire metadata of the copy of the batch file from the remotely located first user device via an Internet connection; compare the metadata of the copy of the batch file to metadata of other batch files locally stored at the collection server; responsive to determining that the metadata does not match the metadata of the other batch files, acquire the copy of the batch file from the remotely located first user device via the Internet connection; and publish information related to the metadata within a dashboard including an identifier of the remotely located first user device from which the copy of the batch file was received.

2. The collection server of claim 1, further comprising instructions stored in the memory that are configured when executed to cause the collection server to: after receiving the copy of the batch file from the user device, transmit a message to the remotely located first user device indicative that the copy of the batch file is to be deleted at the remotely located first user device.

3. The collection server of claim 1, further comprising instructions stored in the memory that are configured when executed to cause the collection server to: responsive to determining that the metadata matches metadata of at least one other batch file, transmit a message to the remotely located first user device indicative that the batch file is to be deleted.

4. The collection server of claim 1, further comprising instructions stored in the memory that are configured when executed to cause the collection server to: aggregate the batch file with other batch files; and transmit the aggregation of the batch files to a host blood processing system to enable the blood donation information to be associated with donated blood.

5. The collection server of claim 1, further comprising instructions stored in the memory that are configured when executed to cause the collection server to: responsive to determining that communication is possible with the local collection device, compare metadata of the batch file to metadata of other batch files locally stored at the collection server; and responsive to determining that the metadata does not match the metadata of the other batch files, acquire the batch file from the local collection device via an Internet connection to the local collection server.

6. The collection server of claim 1, wherein the metadata of the copy of the batch file includes at least one of a number of blood donors, a last update time of the batch file, a file size of the batch file, a file identifier of the batch file, a creation date or time of the batch file, and an identifier of the remotely located first user device.

7. The collection server of claim 1, wherein the Internet connection to the remotely located first user device is over at least one of a cellular network and a wide area network ("WAN") and includes at least one of a secure sockets layer ("SSL") and a virtual private network ("VPN") tunnel.

8. The collection server of claim 1, wherein the remotely located first user device is a registered device with respect to the collection server and the local collection device.

9. The collection server of claim 1, further comprising instructions stored in the memory that are configured when executed to cause the collection server to: responsive to determining that communication is not possible with the local collection device, determine whether communication is possible with a remotely located second user device that is configured to store a second copy of the batch file; responsive to determining that communication is possible with the remotely located second user device, acquire metadata of the second copy of the batch file from the remotely located second user device via an Internet connection; compare the metadata of the second copy of the batch file to the metadata of other batch files, including the metadata of the first copy of the batch file received from the remotely located first user device, which are locally stored at the collection server; and responsive to determining that the metadata of the second copy of the batch file matches the metadata of the first copy of the batch file, transmit a message to the remotely located second user device indicative that the second copy of the batch file is to be deleted.

10. A system for transferring blood donation batch files comprising: a collection device configured to: receive blood donation information from blood donors, store the blood donation information within a blood donation batch file located at a designated directory of a memory, receive or create metadata related to the blood donation information and the blood donation batch file, store the metadata to the blood donation batch file, make the blood donation batch file available at the designated directory, and transmit the blood donation batch file to a trusted registered user device; and a central collection server configured to: determine the trusted registered user device is available for communication via a network connection, after determining that communication is not possible with the collection device and determining the trusted registered user device is connected, acquire the blood donation batch file from the trusted registered user device, and aggregate the blood donation batch file with blood donation batch files received from other trusted registered user devices.

11. The system of claim 10, wherein the trusted registered user device is configured to operate a transfer application configured to: determine whether the trusted registered user device is communicatively coupled to the collection device via a local connection; responsive to determining that the collection device is connected, acquire the blood donation batch file from the designated directory of the collection device, store the blood donation batch file to a memory of the trusted registered user device.

12. The system of claim 11, wherein the transfer application operating on the trusted registered user device is configured to: poll the trusted registered user device for metadata of locally stored blood donation batch files; compare the read metadata to metadata of locally stored blood donation batch files; and responsive to determining that a match does not exist, acquire the blood donation batch file that is associated with the acquired metadata.

13. The system of claim 12, wherein the collection device is communicatively coupled to the trusted registered user device during a first time, and the central collection server is communicatively coupled to the trusted registered user device during a second time subsequent to the first time when the trusted registered user device is no longer connected to the collection device.

14. The system of claim 10, wherein the blood donation information includes at least one of demographic information, blood donor eligibility answers, and blood draw data.

15. The system of claim 10, wherein the collection device is communicatively coupled to the trusted registered user device via at least one of a private wireless local area network, a direct Bluetooth® connection, and a direct near field communication connection, and the trusted registered user device is communicatively coupled to the central collection server via at least one of a cellular network and a WAN.

16. The system of claim 10, wherein the central collection server is configured to: poll the trusted registered user device at predetermined times by reading metadata of blood donation batch files locally stored by the transfer application; compare the read metadata to metadata of locally stored blood donation batch files; responsive to determining that a match does not exist, acquire the blood donation batch file that is associated with the acquired metadata; and transmit a message to the trusted registered user device that causes the transfer application to delete the locally stored blood donation batch file that was transmitted to the central collection server.

17. A method for transferring blood donation batch files comprising: during a first time period: determining via a transfer application operating on a user device that the user device is within communication proximity and available to communicate with an information collection device via a local connection, establishing, via the transfer application, a connection between the transfer application on the user device and the information collection device, reading, via the transfer application, metadata of blood donation batch files located at a designated directory on the information collection device, comparing, via the transfer application, the read metadata to metadata related to blood donation batch files stored on the user device, and responsive to determining that at least some of the read metadata does not match the metadata related to blood donation batch files stored on the user device, acquiring a copy, via the transfer application, of the blood donation batch files at the information collection device that correspond to the un-matched metadata; and during a second time period subsequent to the first time period: determining, via the transfer application, that the user device is communicatively coupled to a collection server via a network connection, transmitting to the collection server, via the transfer application, the metadata related to the blood donation batch files stored on the user device, and responsive to receiving a request message form the collection server indicative of at least one of the blood donation batch files not already present at the collection server, transmitting to the collection server, via the transfer application, the at least one blood donation batch file.

18. The method of claim 17, further comprising after transmitting the at least one blood donation batch file to the collection server, at least one of: (i) deleting the at least one blood donation batch file from storage on the user device, and (ii) moving the at least one blood donation batch file to another memory location unknown by the collection server.

19. The method of claim 17, further comprising configuring the user device with at least one of an address and an identifier of the information collection device to enable the user device to establish a connection with the information collection device.

20. The method of claim 17, further comprising configuring the user device with the designated directory on the information collection device to enable the user device to acquire the copy of the blood donation batch files at the information collection device that correspond to the un-matched metadata.

* * * * *